(12) United States Patent
Keall et al.

(10) Patent No.: US 7,894,571 B2
(45) Date of Patent: Feb. 22, 2011

(54) SYSTEM AND METHOD FOR USING PROSPECTIVE EVALUATION OF DISPLACEMENT AND VELOCITY OF A RESPIRATORY TRACE IN A FIVE DIMENSIONAL PARAMETER SPACE TO REDUCE ARTIFACTS AND DOSAGE IN FOUR DIMENSIONAL COMPUTED TOMOGRAPHY

(75) Inventors: Paul J. Keall, Stanford, CA (US); Ulrich W. Langner, Lexington, KY (US)

(73) Assignee: Stanford University, Palo Alto, CA (US)

( * ) Notice: Subject to any disclaimer, the term of this patent is extended or adjusted under 35 U.S.C. 154(b) by 102 days.

(21) Appl. No.: 12/463,377

(22) Filed: May 8, 2009

(65) Prior Publication Data

US 2009/0310739 A1    Dec. 17, 2009

Related U.S. Application Data

(60) Provisional application No. 61/051,672, filed on May 8, 2008.

(51) Int. Cl.
    *G01N 23/00* (2006.01)

(52) U.S. Cl. .............................................. 378/8; 378/4
(58) Field of Classification Search ..................... 378/4, 378/8, 14, 15, 65
    See application file for complete search history.

(56) References Cited

U.S. PATENT DOCUMENTS

| 2006/0274878 A1* | 12/2006 | Hsieh et al. ..................... 378/8 |
| 2007/0053483 A1* | 3/2007 | Nagata et al. .................. 378/8 |
| 2007/0081704 A1* | 4/2007 | Pan et al. ..................... 382/128 |
| 2009/0067570 A1* | 3/2009 | Mori et al. ..................... 378/8 |

* cited by examiner

*Primary Examiner*—Hoon Song
(74) *Attorney, Agent, or Firm*—Whitham, Curtis, Christofferson & Cook, P.C.

(57) ABSTRACT

A displacement and velocity based prospective cine CT (PDV CT) method is disclosed for starting image acquisition if the displacement and velocity are simultaneously within predetermined tolerances, thus essentially sorting 2D CT images in a five dimensional parameter space, where displacement and the sign of the velocity are used for the temporal sorting, replacing the use of either phase or displacement as the temporal parameter during retrospective sorting, with velocity as a separate parameter correlating to some parameter of the system, e.g. the airflow rate, making it possible to do the image sorting in real-time.

4 Claims, 4 Drawing Sheets

SYSTEM AND METHOD FOR USING PROSPECTIVE EVALUATION OF DISPLACEMENT AND VELOCITY OF A RESPIRATORY TRACE IN A FIVE DIMENSIONAL PARAMETER SPACE TO REDUCE ARTIFACTS AND DOSAGE IN FOUR DIMENSIONAL COMPUTED TOMOGRAPHY

RELATED APPLICATION

This application claims the benefit of U.S. Provisional Application No. 61/051,672 of the same title filed on May 8, 2008.

FEDERALLY-SPONSORED RESEARCH OR DEVELOPMENT

This invention was made with Government support under contract CA116602 awarded by the National Institutes of Health. The Government has certain rights in this invention.

BACKGROUND OF THE INVENTION

1. Field of the Invention

The present invention generally relates to radiation therapy, and in particular to techniques for improving the effectiveness of oncological treatment programs using four dimensional computed tomography (4D CT).

2. Background Description

Respiratory motion creates several problems for thoracic radiology. It degrades anatomic position reproducibility during imaging. It necessitates larger margins during radiotherapy planning. And it causes errors during radiation delivery. Clinically significant lung tumor motion cannot be predicted by any known clinical parameters, suggesting that tumor motion must be explicitly determined for each patient. In fact, recent European Organization for Research and Treatment of Cancer (EORTC) guidelines state that "An assessment of 3D tumor mobility is essential for treatment planning and delivery in lung cancer."

Existing methods to account for respiratory motion during CT imaging include breath-hold, respiratory gating, and 4D CT. Four-dimensional thoracic CT images that account for respiratory motion have successfully been acquired using single-slice scanners, however, the authors of these works acknowledge the temporal and spatial limitations of 4D acquisition with current single-slice technology. Multi-slice 4D CT scans have been acquired using an axial/cine method at Washington University, Memorial Sloan Kettering Cancer Center, and Massachusetts General Hospital and by using a helical method at the MD Anderson Cancer Center. Four-dimensional cone-beam CT scans have been acquired using a benchtop system by Taguchi as well as clinically at the Netherlands Cancer Institute. Four-dimensional CT scans can be used to determine tumor motion and tumor-motion-encompassing treatment volumes—in the absence of respiratory management devices—as well as to employ the data for 4D planning and delivery. Individual phases of the 4D CT scan can be used for respiratory gated radiotherapy planning.

The use of 4D thoracic CT has been developed for and applied to radiation oncology patients. However, high-quality 4D CT data, along with accurate deformable image-registration algorithms to automate analysis of this data, could play an important role in the analysis of lung function for a variety of pulmonary diseases. The changes in local density of the lung as a function of respiration could be automatically detected and the abnormal regions displayed, leading to faster diagnosis.

Current 4D thoracic CT techniques build on those existing for cardiac imaging, in which the cardiac signal is input to the CT scanner during the sinogram evolution, from which image reconstruction at several cardiac phases can occur. However, although successive cardiac cycles are relatively reproducible under non-stressed conditions, a factor limiting the success of 4D thoracic CT is the irregularity of respiratory cycles in both displacement and cycle-to-cycle periods. Irregularity manifests itself as imaging artifacts, leading to anatomical mismatches, or there is insufficient acquisition of projection data to reconstruct a full image.

To reduce this irregularity, audio and audiovisual breathing-training methods have been applied to try to improve the quality of 4D thoracic CT data. However, even with audiovisual breathing training, respiration irregularities remain. Thus, whilst taking a similar approach to 4D cardiac CT methods is a good first approximation, further development is necessary to improve 4D CT acquisition.

Four-dimensional computed tomography (4D CT) acquisition methods that explicitly account for respiratory motion have been developed recently in academic and commercial settings. 4D CT is generally acquired either by sinogram or image sorting based on a post-acquisition procedure using external respiration signals. The patient's ability to maintain reproducible respiratory signals is the limiting factor during 4D CT. Methods of breathing coaching, e.g., audiovisual biofeedback, can improve respiration reproducibility, however, significant variations remain and cause artifacts in the 4D CT scan.

Mismatches in displacement or phase of a patient's respiratory signal corresponding to two dimensional (2D) images taken at subsequent couch positions become visible as artifacts in reconstructed 4D CT images. These artifacts appear as undefined or irregular boundaries in the 4D CT images and cause systematic errors in patient contouring and dose calculations. Another concern is the substantially higher dose necessary for 4D CT, which increases approximately by a factor of ten (depending on the average respiratory period for each patient) when compared to 3D CT.

SUMMARY OF THE INVENTION

It is therefore an object of the present invention to provide a method for reducing artifacts in 4D CT images.

Another object of the invention is to provide a method of reducing dosage in radiation therapy based on 4D CT.

A further object of the invention is to provide a method of 4D CT based therapy that reduces data storage requirements.

It is also an object of the invention to enable use of simulation of similar respiratory motion of the patient during treatment as in a planning scan with breathing training.

It is yet another object of the invention to provide a simulation strategy that will be applicable to multi-slice scanners which can scan the complete region of interest.

Another object of the invention is to provide prospective displacement/velocity (PDV) CT images that are not dependent on the regularity of respiratory motion.

A further object of the invention is to avoid the difficulties associated with real-time phase estimation.

Yet another object of the invention is to provide a treatment program for 4D CT that is flexible and robust in the sense that by varying the parameters the efficiency and accuracy can be enhanced/decreased depending on the application.

It is also an object of the invention to eliminate the need for post processing of images.

The invention provides a displacement and velocity based prospective cine CT (PDV CT) method to start image acquisition if the displacement and velocity of a respiratory signal are simultaneously within predetermined tolerances, thus essentially sorting 2D CT images in a five dimensional parameter space by using the three spatial dimensions, a temporal parameter, and a parameter to indicate the 'state' of the system. Displacement and the sign of the velocity are used as the temporal sorting parameter, replacing the use of either phase or displacement as the temporal parameter during retrospective sorting, with velocity as a separate parameter correlating to some parameter of the system, e.g. the airflow rate. The use of velocity (df/dt) of the respiratory signal (f(t)), instead of the more commonly used phase, makes it possible to do the image sorting in real-time, instead of retrospectively, because the problem with accurate online phase calculation is avoided.

An aspect of the invention is a method for reducing motion artifacts and patient dose in radiological imaging using four dimensional computed tomography (4D CT). The method is implemented using equipment that obtains a signal corresponding to periodic motion of an anatomy of the patient, and also obtaining a reference signal representing an average for the patient of this signal. A prospective 4D CT controller is used to control a 4D CT scanner beam so that the beam is on and recording images of the anatomy only when both a displacement and a velocity of the signal are simultaneously within predetermined tolerances in comparison to the reference signal. In real time, during the scan which generates the images, the images are sorted using the velocity as a parameter. The sorted images are then saved, typically on computer storage media, for post processing development of a treatment planning system for radiation therapy on the anatomy of the patient. The controller and the image sorting may be implemented in computer software or a combination of computer hardware and software.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
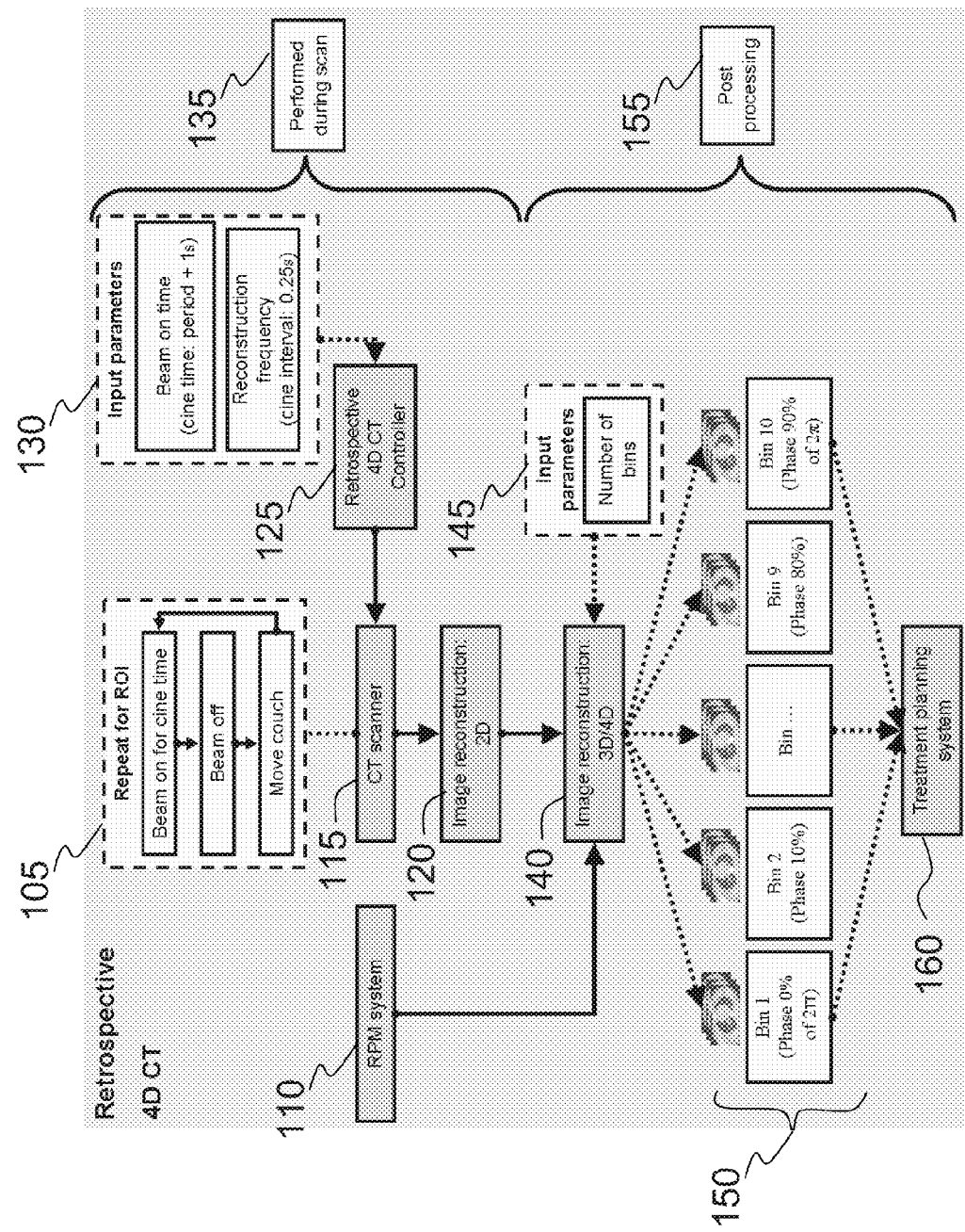
FIG. 1 is a schematic showing the current retrospective 4D CT image-acquisition procedure.
Figure 2:
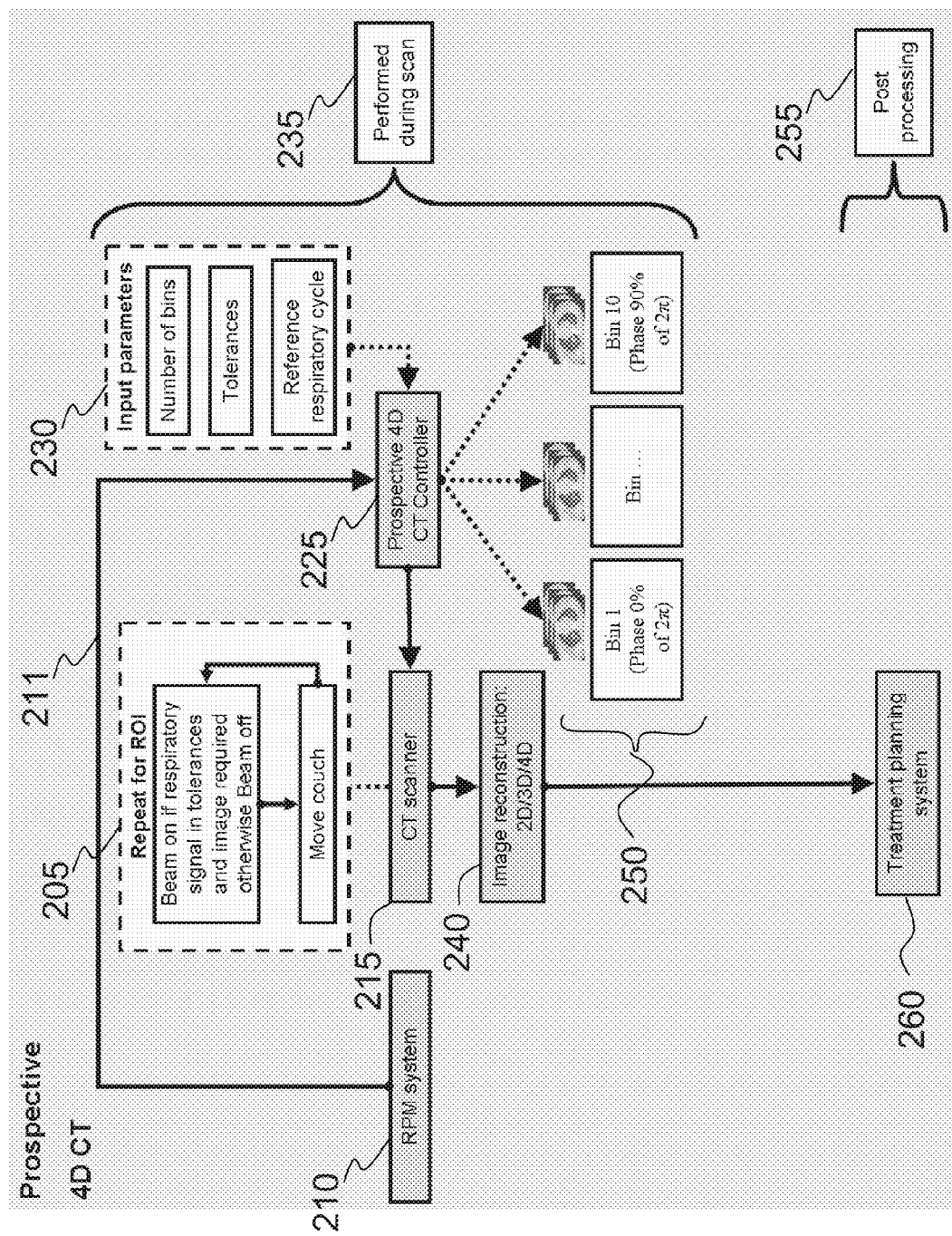
FIG. 2 is a schematic showing PDV CT image acquisition using respiration input to the control in order to reduce motion artifacts.

In FIG. 1 the current retrospective processes are illustrated. These current processes may be compared to the PDV CT method of the invention as shown in FIG. 2. In FIG. 1, retrospective methods acquire a respiratory signal with a Varian Real Time Position Management (RPM) system 110 simultaneously with the 2D CT image acquisition 120 using CT scanner 115. For the CT acquisition, data are acquired for a finite time (the time it takes the gantry to rotate through 180°+the fan angle; ~0.39 s for a gantry rotation of 0.5 s), under control of controller 125 using input parameters 130, for each image, repeated 105 for each region of interest (ROI), implying that if the RPM 110 acquire data at 30 Hz then each image is acquired during 13 data points of the RPM signal. All this is performed during the scan 135. Then, during post processing 155, images are reconstructed 140 every 0.25 s (the cine time) for the average respiratory period+1 s, e.g. 20 images for a 4 s respiratory period. These images are then retrospectively sorted into phase or displacement bins 150, according to input parameters 145, by matching the time stamps, to develop a treatment planning system 160.

During the PDV CT method shown in FIG. 2, the bins are predetermined from a calculated average respiratory wave form for each patient, the reference wave. This reference wave will then be used to determine in real-time, using prospective 4D CT controller 225, if the respiratory signal 211 from the RPM system 210 is within tolerance, for both displacement and velocity, and if an image is needed for the bin (in principal any respiratory signal can be used, e.g. a signal from a spirometer). The number of bins, tolerances, and a patient reference respiratory signal are represented within input parameters 230. A signal is sent to the scanner 215 to start acquisition only if both these conditions are met. However, acquisition can stop any time if these conditions are not met and an image is marked as recorded successfully only if these conditions were met continuously for ~0.39 s (see above). As with retrospective methods, this process is repeated 205 for each ROI. In contrast to retrospective methods, image reconstruction 240 and sorting into bins 250 is performed during the scan 235. Only development of the treatment planning system 260 is left to post-processing 255.

Because this interface between software and the CT scanner does not currently exist, this method could not be tested directly. In this study it is therefore assumed that the tumor motion (or any anatomical motion caused by respiratory motion) correlates to respiratory motion and therefore the feasibility of the method can be assessed by the respiratory signals alone, i.e. scaled differences in displacement of the respiratory signal between subsequent couch positions will correspond to differences in the relevant anatomical structure.

Respiratory signals of 24 lung cancer patients (103 fractions) under free breathing conditions were used as input to study the efficiency of the respective 4D CT acquisition methods. To overcome system latency and enhance efficiency a linear adaptive prediction algorithm was used. The RMS of the difference between the displacements and velocities, respectively, of the respiratory signal corresponding to subsequent images was calculated in order to evaluate the accuracy of each method. The number of couch positions that could be completed, i.e. images for all the bins could be acquired for the couch position, for each method was calculated as proxy for the time efficiency of the scan. The length of time for which the x-ray beam is turned on is calculated for each method as proxy of the dose that a patient will receive. This was also done for different model parameters, such as changes in the percentage of image points that must be tested, different methods for performing the sorting with PDV CT, different displacement and velocity tolerances, etc.

These model parameters are varied to enhance a certain aspect of PDV CT, e.g. if the dose must be decreased the percentage of image points that must be tested can be decreased, because this will increase the possibility that an image is acquired with the current data. This may, however, have a negative impact on the accuracy and/or on the scan time. Note that there is still ~0.39 s of data continuously acquired for the image, but that only a certain percentage is tested against the tolerances.

Results and Discussion

Figure 3:
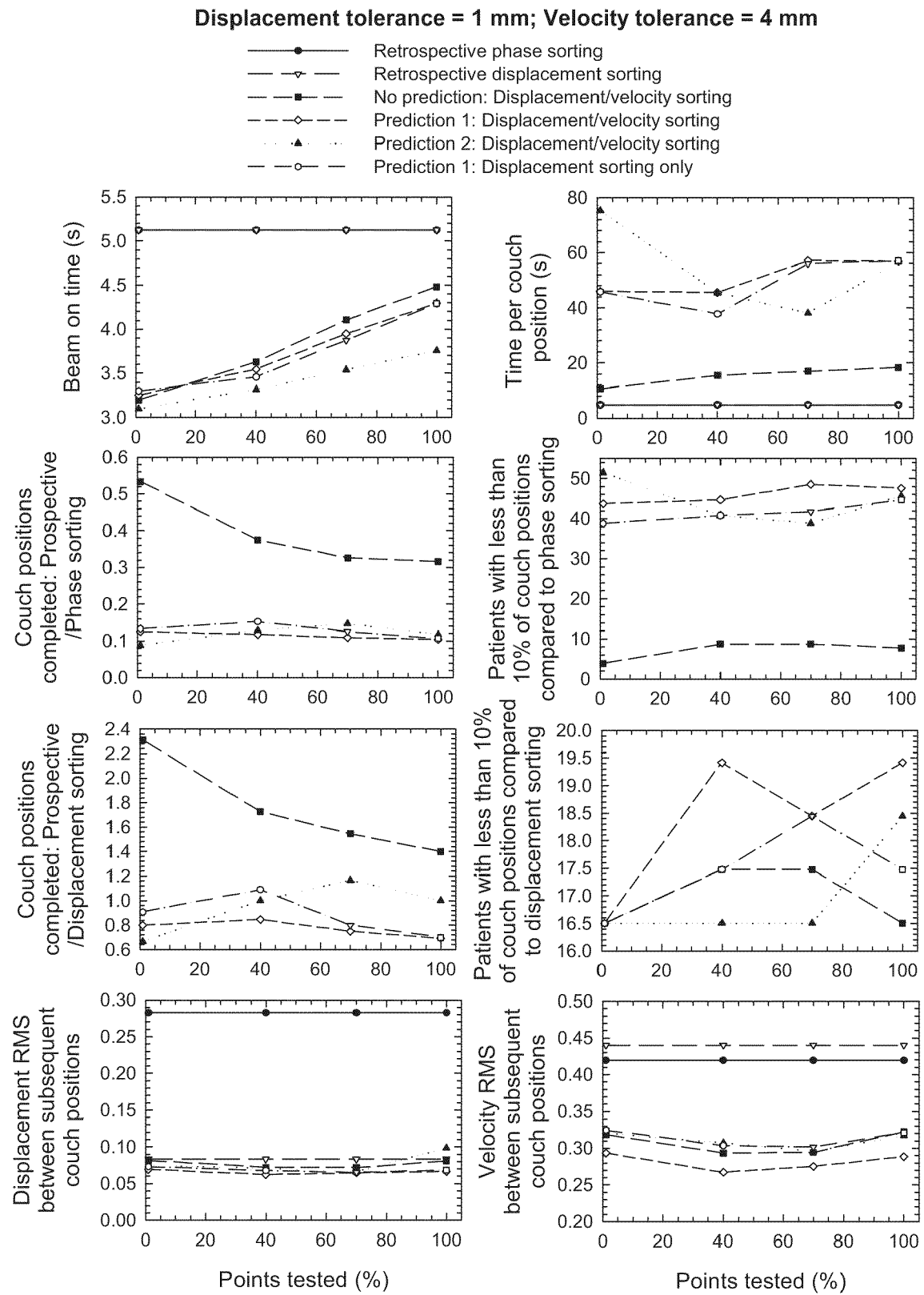
FIG. 3 is a series of graphs showing efficiency of the PDV CT technique in acquisition time, dose, and accuracy as a function of the percentage of image points tested.
Figure 4:
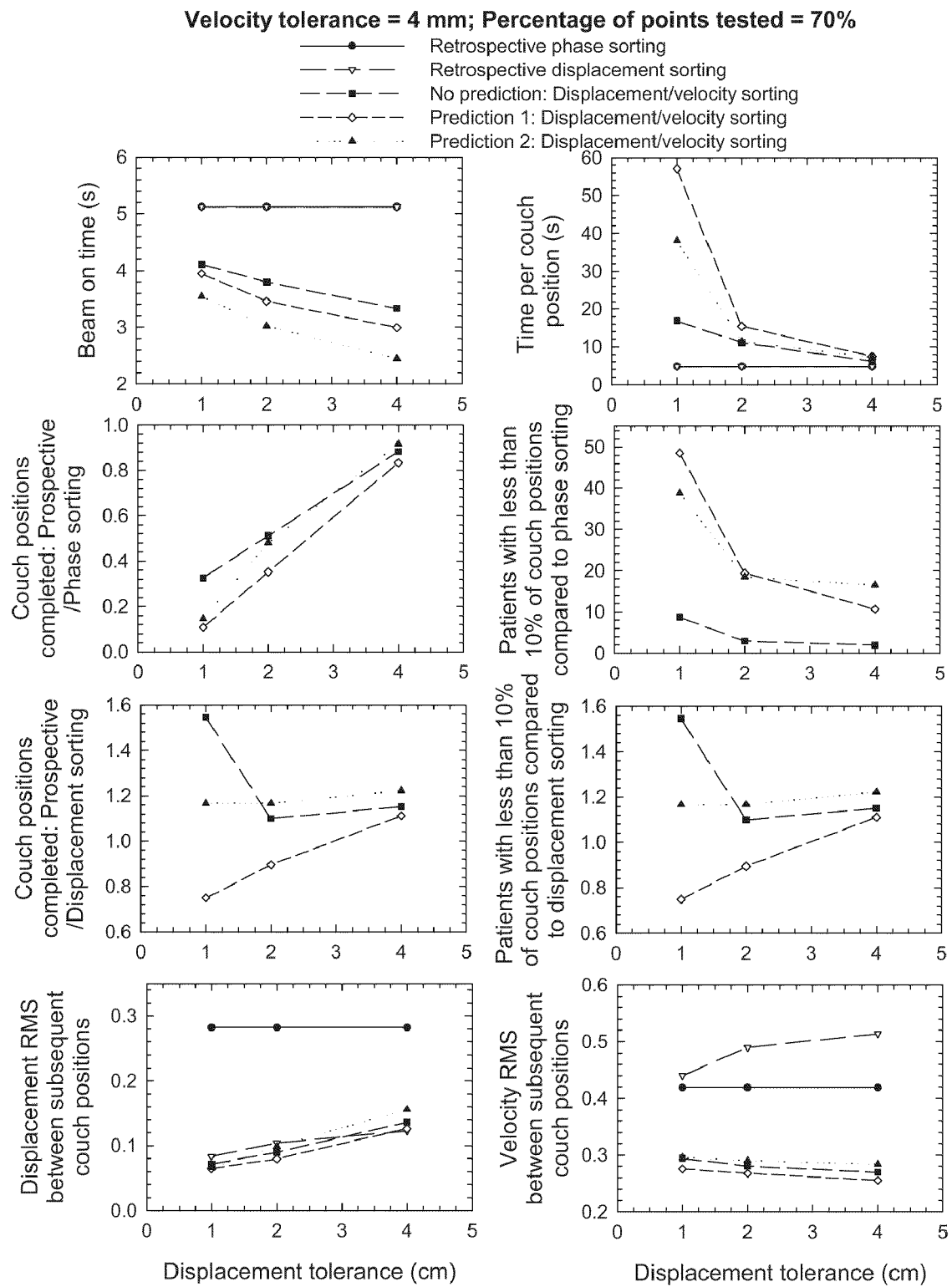
FIG. 4 is a series of graphs showing efficiency of the PDV CT technique in acquisition time, dose, and accuracy as a function of displacement tolerance.

In FIG. 3 the model efficiency in acquisition time, beam-on-time, and accuracy are shown in a series of graphs as a function of the percentage of image points tested. The displacement and velocity tolerances were kept constant at 1 mm and 4 mm/s, respectively. In FIG. 4 the model efficiency in acquisition time, dose, and accuracy are shown in a series of graphs as a function of the displacement tolerance. The velocity tolerance was kept constant at 4 mm/s and the percentage of points tested was kept constant at 70%.

The legend for the graphs in FIG. 3 and FIG. 4 may be interpreted using Table 1, below. This table describes the following legend lines used to show the data on each of the graphs: a) retrospective phase sorting and b) retrospective displacement sorting of the prior art technique described in FIG. 1; the PDV CT technique described in FIG. 2, using displacement/velocity sorting c) with no prediction; if it is predicted that all points will stay in tolerance, d) test current respiratory signal data point against corresponding point of reference bin, and e) calculate mean from all the points needed for an image (consisting of respiratory signal data points already recorded for image and the predicted points still needed) and test it against mean of reference bin; and f) for PDV CT with Prediction 1, but done only for displacement sorting. The values are the means over 24 patients (103 fractions) and 10 bins.

From FIG. 4 it follows that the displacement accuracy will improve as the displacement tolerance is decreased, although the beam-on-time will increase. Interestingly, the velocity accuracy increases as the displacement tolerance decreases. The acquisition time increase exponentially as the displacement tolerance decreases.

Advantages of PDV CT Method

1. Fewer artifacts in 4D CT images,
2. Less dosage,
3. Less data stored,
4. Similar respiratory motion of the patient could be simulated during treatment as in the planning scan with breathing training (this also ensures that this method will still be applicable even if multislice scanners which can scan the complete region of interest at once are used),
5. Quality of PDV CT images are not dependent on the regularity of respiratory motion (although the efficiency will enhance the more regular it gets),
6. Real-time phase estimation is avoided,
7. Flexibility and robustness in the sense that by varying the parameters the efficiency and accuracy can be enhanced/decreased depending on the application (treatment planning or diagnostic),

TABLE 1

| Figure legend | Model description |
|---|---|
| Retrospective sorting methods | |
| a) Retrospective phase sorting | Images sorted according to phase retrospectively |
| b) Retrospective displacement sorting | Images sorted according to displacement retrospectively |
| PDV CT sorting methods | |
| c) No Prediction: Displacement/Velocity sorting | Only current respiratory signal data point tested against tolerances |
| d) Prediction 1: Displacement/Velocity sorting | Start image acquisition if it is predicted that all points will stay in tolerance. During image acquisition: Test current respiratory signal data point against corresponding point of reference bin |
| e) Prediction 2: Displacement/Velocity sorting | Start image acquisition if it is predicted that all points will stay in tolerance. During image acquisition: Calculate mean from all the points needed for an image (consisting of respiratory signal data points already recorded for image and the predicted points still needed) and test it against mean of reference bin. |
| f) Prediction 1: Displacement sorting only | Same as Prediction 1 above, but done only for displacement sorting, i.e. the velocity tolerance was arbitrarily large, although the sign is still used in order to differentiate between exhale and inhale. |

From FIGS. 3 and 4 it follows that the 'no prediction' scenario for the PDV CT produces the fastest scans, although accuracy and beam-on-time are the worst. The Prediction 2 scenario, on the other hand, produces the least beam-on-time but also less accuracy. As expected, the beam-on-time as well as the acquisition time increased linearly as it became, more difficult to acquire an image, i.e. as the percentage of points tested increased, although this was not the case for the accuracy, where a minimum was observed if 40%-60% of the points were tested.

8. No post processing of images required.
9. PDV CT may become especially important if proton treatment, where accuracy is essential, is used.

CONCLUSIONS

The PDV CT method described here, which does image sorting in 5D parameter space, could be a valuable tool for reducing artifacts in 4D CT images, and more importantly, substantial dose reduction to the patient, although the price may be acquisition time.

Having thus described our invention, what we claim as new and desire to secure by Letters Patent is as follows:

1. A method for reducing motion artifacts and patient dose in radiological imaging using four dimensional computed tomography (4D CT), comprising the steps of:
   obtaining a signal corresponding to periodic motion of an anatomy of the patient;
   obtaining a reference signal representing an average for said patient of said signal;
   controlling a 4D CT scanner beam so that the beam is on and recording images of the anatomy only when both a displacement and a velocity of said signal are simultaneously within predetermined tolerances in comparison to said reference signal;
   sorting the 4D CT images in real time using said velocity; and
   saving the sorted images for development of a treatment planning system for radiation therapy on said anatomy of the patient.

2. A method as in claim 1, wherein said anatomy is a lung and said signal is a respiratory signal.

3. A system for reducing motion artifacts and patient dose in radiological imaging using four dimensional computed tomography (4D CT), comprising:
   means for obtaining a signal corresponding to periodic motion of an anatomy of the patient;
   means for obtaining a reference signal representing an average for said patient of said signal;
   means for controlling a 4D CT scanner beam so that the beam is on and recording images of the anatomy only when both a displacement and a velocity of said signal are simultaneously within predetermined tolerances in comparison to said reference signal;
   means for sorting the 4D CT images in real time using said velocity; and
   means for saving the sorted images for development of a treatment planning system for radiation therapy on said anatomy of the patient.

4. A system as in claim 3, wherein said anatomy is a lung and said signal is a respiratory signal.

\* \* \* \* \*